United States Patent
Buiser et al.

(10) Patent No.: US 9,050,092 B2
(45) Date of Patent: *Jun. 9, 2015

(54) EMBOLIC COILS

(75) Inventors: Marcia S. Buiser, Watertown, MA (US); Ashley Seehusen, Newton, MA (US); Christopher Nardone, N. Chelmsford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/442,321

(22) Filed: Apr. 9, 2012

(65) Prior Publication Data

US 2012/0215297 A1    Aug. 23, 2012

Related U.S. Application Data

(63) Continuation of application No. 11/430,602, filed on May 9, 2006, now Pat. No. 8,152,839, which is a continuation-in-part of application No. 11/311,617, filed on Dec. 19, 2005, now Pat. No. 8,101,197.

(51) Int. Cl.
| | | |
|---|---|---|
| *A61F 2/02* | (2006.01) | |
| *A61F 2/06* | (2013.01) | |
| *A61F 2/88* | (2006.01) | |
| *A61M 29/00* | (2006.01) | |
| *A61B 17/12* | (2006.01) | |
| *A61B 19/00* | (2006.01) | |
| *A61B 17/00* | (2006.01) | |

(52) U.S. Cl.
CPC ..... *A61B 17/12022* (2013.01); *A61B 17/12113* (2013.01); *A61B 17/12145* (2013.01); *A61B 17/1215* (2013.01); *A61B 19/54* (2013.01); *A61B 2017/00004* (2013.01); *A61B 2017/00526* (2013.01); *A61B 2017/00867* (2013.01); *A61B 2017/00893* (2013.01)

(58) Field of Classification Search
None
See application file for complete search history.

(56) References Cited

U.S. PATENT DOCUMENTS

| | | | | |
|---|---|---|---|---|
| 6,280,457 | B1 * | 8/2001 | Wallace et al. | 606/200 |
| 7,896,899 | B2 * | 3/2011 | Patterson et al. | 606/200 |
| 8,152,839 | B2 * | 4/2012 | Buiser et al. | 623/1.11 |
| 2005/0021074 | A1 * | 1/2005 | Elliott | 606/200 |
| 2006/0200190 | A1 * | 9/2006 | Lorenzo et al. | 606/200 |
| 2008/0195139 | A1 * | 8/2008 | Donald et al. | 606/200 |

* cited by examiner

*Primary Examiner* — Shanon A Foley
(74) *Attorney, Agent, or Firm* — Kacvinsky Daisak Bluni PLLC

(57) ABSTRACT

Coils, such as embolic coils, and related methods, devices, and compositions, are disclosed.

12 Claims, 18 Drawing Sheets

EMBOLIC COILS

CROSS-REFERENCE TO RELATED APPLICATIONS

This application is a continuation of U.S. patent application Ser. No. 11/430,602, filed May 9, 2006, now U.S. Pat. No. 8,152,839 issued Mar. 21, 2012, which is a continuation-in-part of U.S. patent application Ser. No. 11/311,617, filed Dec. 19, 2005, now U.S. Pat. No. 8,101,197, issued Jan. 24, 2012, which are hereby incorporated by reference in their entirety.

TECHNICAL FIELD

The invention relates to coils, such as embolic coils, as well as related methods, devices, and compositions.

BACKGROUND

Therapeutic vascular occlusions (embolizations) are used to prevent or treat pathological conditions in situ. Embolic coils can be used to occlude vessels in a variety of medical applications. Delivery of embolic coils (e.g., through a catheter) can depend on the size and/or shape of the coils. Some embolic coils include fibers that can, for example, enhance thrombosis at a treatment site.

SUMMARY

In one aspect, the invention features a wound ribbon in the shape of an embolic coil.

In another aspect, the invention features a method of making an embolic coil that includes winding a ribbon into the shape of an embolic coil.

In an additional aspect, the invention features a medical device including a tubular body and at least one wound ribbon (e.g., a plurality of wound ribbons) that is in the shape of an embolic coil. The tubular body has a lumen and the wound ribbon is disposed within the lumen.

In a further aspect, the invention features a method that includes administering at least one wound ribbon (e.g., a plurality of wound ribbons) to a subject. The wound ribbon is in the shape of an embolic coil.

In another aspect, the invention features a method of using a medical device that includes a tubular body and at least one wound ribbon that is in the shape of an embolic coil. The tubular body has a lumen and the wound ribbon is disposed within the lumen. The method includes inserting the tubular body into a lumen of a subject, and delivering the wound ribbon into the lumen of the subject.

Embodiments can include one or more of the following features.

In some embodiments, the wound ribbon can include two ends, each of which is not attached to a medical device (e.g., a catheter) or a medical device component (e.g., a guidewire). In certain embodiments, the embolic coil can include two ends, and the method may not include attaching either of the ends to a medical device (e.g., a catheter) or a medical device component (e.g., a guidewire).

In some embodiments, the wound ribbon can include first and second windings. In certain embodiments, the first winding can contact the second winding. In some embodiments, the wound ribbon can include more than two windings (e.g., at least five windings, at least ten windings, at least 15 windings, at least 20 windings, at least 50 windings, at least 100 windings).

In certain embodiments, the ribbon can have a polygonal transverse cross-section. For example, the ribbon can have a rectangular transverse cross-section with a width and a length that is longer than the width. The length of the rectangular transverse cross-section can be at least 0.001 inch (e.g., at least 0.0015 inch, at least 0.002 inch, at least 0.003 inch, at least 0.004 inch, at least 0.005 inch) and/or at most 0.006 inch (e.g., at most 0.005 inch, at most 0.004 inch, at most 0.003 inch, at most 0.002 inch, at most 0.0015 inch). In some embodiments, the length of the rectangular transverse cross-section can be 0.002 inch. The width of the rectangular transverse cross-section can be at least 0.0005 inch (e.g., at least 0.001 inch, at least 0.0015 inch, at least 0.002 inch, at least 0.003 inch, at least 0.004 inch, at least 0.0045 inch) and/or at most 0.005 inch (e.g., at most 0.0045 inch, at most 0.004 inch, at most 0.003 inch, at most 0.002 inch, at most 0.0015 inch, at most 0.001 inch). In certain embodiments, the width of the rectangular transverse cross-section can be 0.001 inch. In some embodiments, the ratio of the length of the rectangular cross-section to the width of the rectangular cross-section can be at least 1:1 (e.g., at least about 1.25:1, at least about 2:1, at least about 5:1, at least about 10:1, at least about 20:1, at least about 30:1, at least about 50:1) and/or at most about 75:1 (e.g., at most about 50:1, at most about 30:1, at most about 20:1, at most about 10:1, at most about 5:1, at most about 2:1, at most about 1.25:1). In certain embodiments, the ratio of the length of the rectangular cross-section to the width of the rectangular cross-section can be about 2:1. In some embodiments, the ribbon can have a square transverse cross-section.

In certain embodiments, the wound ribbon can include at least one fiber (e.g., a plurality of fibers). In some embodiments, the wound ribbon can include two windings and at least one fiber that is disposed between the two windings. The fiber may include a polyester (e.g., polyethylene terephthalate) and/or a polyamide (e.g., nylon).

In some embodiments, the wound ribbon can include a metal (e.g., platinum), a metal alloy (e.g., stainless steel, Nitinol), and/or a polymer. In certain embodiments, the wound ribbon can include a radiopaque material. In some embodiments, the wound ribbon can include a polymer and a radiopaque material that is disposed in the polymer.

In certain embodiments, the embolic coil can have a primary shape with an outer diameter of at least 0.003 inch (e.g., at least 0.005 inch, at least 0.01 inch, at least 0.012 inch, at least 0.015 inch, at least 0.02 inch, at least 0.03 inch, at least 0.035 inch) and/or at most 0.038 inch (e.g., at most 0.035 inch, at most 0.03 inch, at most 0.02 inch, at most 0.015 inch, at most 0.012 inch, at most 0.01 inch, at most 0.005 inch). In some embodiments, the embolic coil can have a primary shape with an inner diameter of at least 0.001 inch (e.g., at least 0.002 inch, at least 0.004 inch, at least 0.005 inch, at least 0.01 inch, at least 0.015 inch, at least 0.02 inch, at least 0.025 inch, at least 0.03 inch, at least 0.035 inch) and/or at most 0.036 inch (e.g., at most 0.035 inch, at most 0.03 inch, at most 0.025 inch, at most 0.02 inch, at most 0.015 inch, at most 0.01 inch, at most 0.005 inch, at most 0.004 inch, at most 0.002 inch).

In some embodiments, winding a ribbon into the shape of an embolic coil can include forming first and second windings out of at least a portion of the ribbon. In certain embodiments, the first winding can contact the second winding. In some embodiments, the method can include disposing at least one fiber between the first and second windings.

In certain embodiments, winding a ribbon into the shape of an embolic coil can include winding the ribbon around a mandrel. The mandrel can have an outer diameter of at least 0.001 inch (e.g., at least 0.004 inch, at least 0.01 inch, at least 0.02 inch, at least 0.03 inch) and/or at most 0.033 inch (e.g., at most 0.03 inch, at most 0.02 inch, at most 0.01 inch, at most 0.004 inch).

In some embodiments, the medical device can further include a pusher wire. The pusher wire can be disposed within the lumen of the tubular body and/or can contact the wound ribbon.

In certain embodiments, the tubular body can be a catheter. In some embodiments, the tubular body can be an introducer sheath.

The method may be used to treat at least one of the following conditions: aneurysms, arteriovenous malformations, traumatic fistulae, and tumors. In certain embodiments, the method can include embolizing a lumen of a subject.

Embodiments can include one or more of the following advantages.

In some embodiments, an embolic coil can retain fibers relatively well (e.g., as the embolic coil is advanced and/or retracted during placement at a target site). For example, in certain embodiments, an embolic coil may include windings that contact each other. This contact between the windings can enhance the ability of the embolic coil to retain fibers that are disposed between the windings. This can be advantageous, for example, because it can reduce the likelihood of fibers dissociating from the embolic coil (e.g., during delivery to a target site) and traveling to a non-target site.

In certain embodiments, the structure of an embolic coil can be such that the embolic coil has a relatively high radiopacity. In some embodiments in which an embolic coil has a relatively high radiopacity, the embolic coil can exhibit enhanced visibility under X-ray fluoroscopy (e.g., when the embolic coil is in a subject). In certain embodiments, an embolic coil with a relatively high radiopacity can be viewed using X-ray fluoroscopy (e.g., by a physician and/or a technician) without using a radiopaque contrast agent. An embolic coil with a relatively high radiopacity may be viewed using a non-invasive technique, and/or may be monitored to determine the progress of a procedure and/or to determine whether the embolic coil is migrating to a site that is not targeted for treatment.

In some embodiments, an embolic coil that is formed of a wound ribbon may be easier to maneuver (e.g., during delivery and/or at a target site) than an embolic coil of a comparable size that is not formed of a wound ribbon. As an example, in certain embodiments, an embolic coil that is formed of a wound ribbon can have a relatively high effective column strength, which can cause the embolic coil to have relatively good pushability and to be relatively stable and easy to deliver to a target site. As another example, in some embodiments, an embolic coil that is formed of a wound ribbon can be relatively flexible. As an additional example, in certain embodiments, an embolic coil that is formed of a wound ribbon can have relatively good secondary shape retention. Thus, the embolic coil can, for example, assume its secondary shape relatively easily after delivery to a target site. The maneuverability of an embolic coil that is formed of a wound ribbon can, for example, allow the embolic coil to be relatively easily packed into a target site, and/or can allow the embolic coil to conform relatively easily to the shape of the target site.

In certain embodiments, an embolic coil that is formed of a wound ribbon may have a relatively smooth outer surface. The relatively smooth outer surface may enhance the deliverability of the embolic coil from a delivery device because, for example, there may be relatively little friction between the embolic coil and the walls of the delivery device if the embolic coil contacts the walls of the delivery device during delivery.

Other aspects, features, and advantages are in the description, drawings, and claims.

DETAILED DESCRIPTION

Figure 1A:
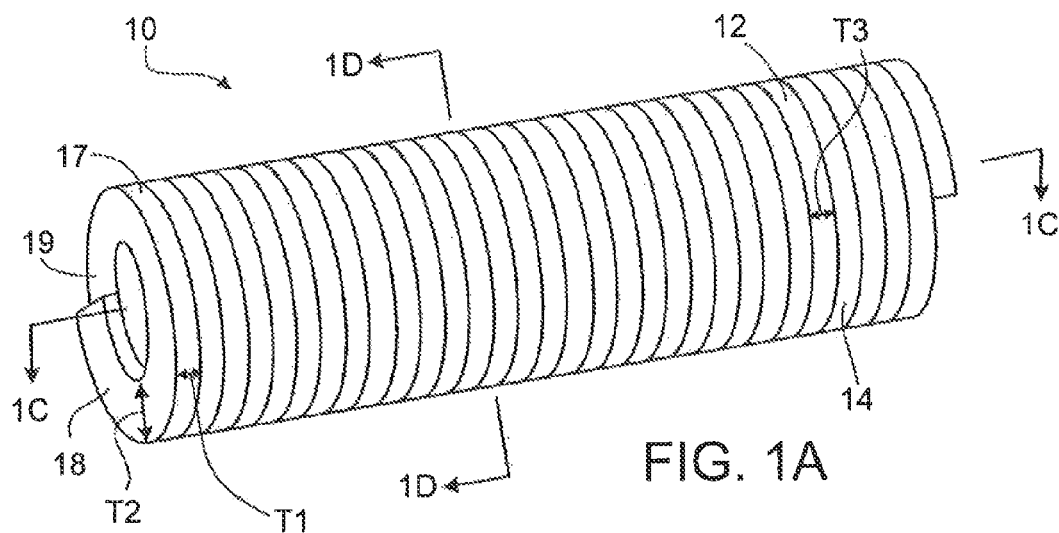
FIG. 1A is a perspective view of an embodiment of an embolic coil.
Figure 1B:
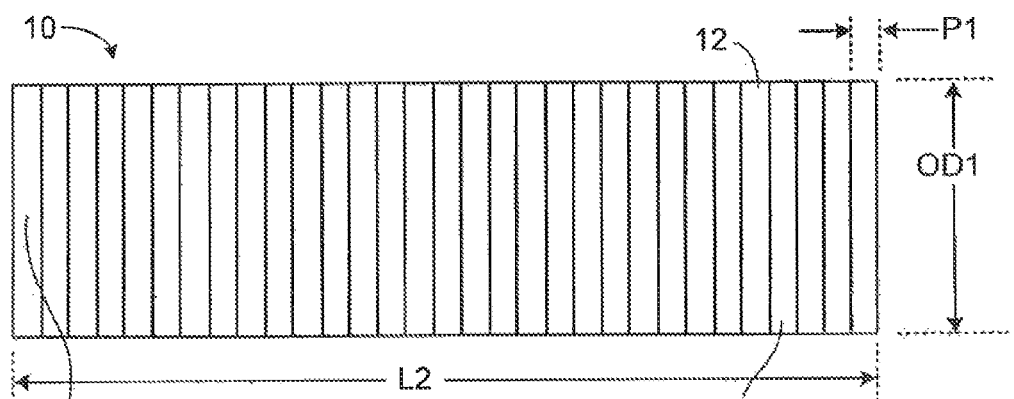
FIG. 1B is a side view of the embolic coil of FIG A.
Figure 1C:
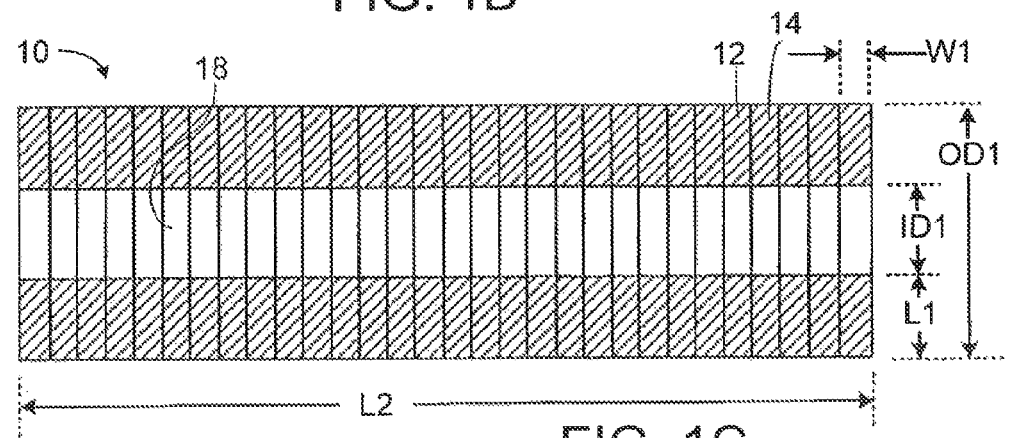
FIG. 1C is a side cross-sectional view of the embolic coil of FIG. 1A, taken along line 1C-1C.

FIGS. 1A-1D show the primary shape of an embolic coil 10 that is formed of windings of a ribbon 18. Consecutive windings of ribbon 18, such as windings 12 and 14, contact each other. As used herein, a ribbon refers to a strip of material having a non-circular transverse cross-section, such as a polygonal transverse cross-section (a transverse cross-section that is a closed plane figure bounded by straight lines). As shown in FIG. 1C, ribbon 18 has a rectangular transverse cross-section with a width W1 and a length L1 that is longer than width Wi.

In some embodiments, length L1 can be at least 0.001 inch (e.g., at least 0.0015 inch, at least 0.002 inch, at least 0.003 inch, at least 0.004 inch, at least 0.005 inch) and/or at most 0.006 inch (e.g., at most 0.005 inch, at most 0.004 inch, at most 0.003 inch, at most 0.002 inch, at most 0.0015 inch). For example, length L1 may be 0.002 inch. In certain embodiments, width W1 can be at least 0.0005 inch (e.g., at least 0.001 inch, at least 0.0015 inch, at least 0.002 inch, at least 0.003 inch, at least 0.004 inch, at least 0.0045 inch) and/or at most 0.005 inch (e.g., at most 0.0045 inch, at most 0.004 inch, at most 0.003 inch, at most 0.002 inch, at most 0.0015 inch, at most 0.001 inch). For example, width W1 may be 0.001 inch.

In some embodiments, as the ratio of length L1 to width W1 increases, the stability of embolic coil 10 can increase, and/or the likelihood of embolic coil 10 retaining its shape (e.g., during delivery to a target site) can increase. In certain embodiments, as the ratio of length L1 to width W1 decreases, the flexibility of embolic coil 10 can increase. In some embodiments, the ratio of length L1 to width W1 can be selected so that embolic coil 10 has good stability, shape retention, and/or flexibility. An embolic coil having one or more of these properties may be relatively easy to deliver to, and/or pack into, a target site (e.g., an aneurysmal sac).

In certain embodiments, the ratio of length L1 to width W1 can be at least 1:1 (e.g., at least about 1.25:1, at least about 1.5:1, at least about 2:1, at least about 5:1, at least about 10:1, at least about 15:1, at least about 20:1, at least about 30:1, at least about 40:1, at least about 50:1, at least about 60:1, at least about 70:1), and/or at most about 75:1 (e.g., at most about 70:1, at most about 60:1, at most about 50:1, at most about 40:1, at most about 30:1, at most about 20:1, at most about 15:1, at most about 10:1, at most about 5:1, at most about 2:1, at most about 1.5:1, at most about 1.25:1) For example, the ratio of length L1 to width W1 may be about 2:1.

As shown in FIG. 1A, ribbon 18 has a side 17 having a relatively small thickness T1 and a side 19 having a relatively large thickness T2. Generally, thickness T1 can be equal to width W1, and thickness T2 can be equal to length L1.

Typically, ribbon 18 can be formed of one or more materials that are capable of being shaped into a coil form. For example, ribbon 18 may be formed of one or more materials that have sufficient flexibility and/or malleability to be shaped into a coil form.

In some embodiments, ribbon 18 can be formed of one or more metals or metal alloys, such as platinum, a platinum alloy (e.g., platinum-tungsten alloy), stainless steel, Nitinol, or Elgiloy® alloy (from Elgiloy Specialty Materials). In certain embodiments, ribbon 18 can be formed of one or more polymers. Examples of polymers include polyolefins, polyurethanes, block copolymers, polyethers, and polyimides. Other examples of polymers are disclosed, for example, in Buiser et al., U.S. patent application Ser. No. 11/311,617, filed on Dec. 19, 2005, and entitled "Coils", which is incorporated herein by reference. In some embodiments, ribbon 18 can be formed out of one or more shape-memory materials, such as Nitinol and/or shape-memory polymers. Examples of shape-memory polymers include shape-memory polyurethanes and the Veriflex™ two-part thermoset shape-memory polymer resin system (from CRG Industries, Dayton, Ohio).

In some embodiments, it may be desirable to observe ribbon 18 using X-ray fluoroscopy. In certain embodiments, ribbon 18 can include one or more radiopaque materials that may enhance the visibility of ribbon 18 under X-ray fluoroscopy. As an example, ribbon 18 may be formed of a radiopaque material. As another example, ribbon 18 may be formed of a material (e.g., a polymer) that encapsulates a radiopaque material, and/or may be formed of a material (e.g., a polymer) within which a radiopaque material is disposed. As an additional example, ribbon 18 may include a coating of a radiopaque material.

As used herein, a radiopaque material refers to a material having a density of about ten grams per cubic centimeter or greater (e.g., about 25 grams per cubic centimeter or greater, about 50 grams per cubic centimeter or greater). A radiopaque material can be, for example, a metal (e.g., tungsten, tantalum, platinum, palladium, lead, gold, titanium, silver), a metal alloy (e.g., stainless steel, an alloy of tungsten, an alloy of tantalum, an alloy of platinum, an alloy of palladium, an alloy of lead, an alloy of gold, an alloy of titanium, an alloy of silver), a metal oxide (e.g., titanium dioxide, zirconium oxide, aluminum oxide), bismuth subcarbonate, or barium sulfate. In some embodiments, a radiopaque material is a radiopaque contrast agent. Examples of radiopaque contrast agents include Omnipaque™, Renocal®, iodiamide meglumine, diatrizoate meglumine, ipodate calcium, ipodate sodium, iodamide sodium, iothalamate sodium, iopamidol, and metrizamide. Radiopaque contrast agents are commercially available from, for example, Bracco Diagnostic. Radiopaque materials are described, for example, in Rioux et al., U.S. Patent Application Publication No. US 2004/0101564 A1, published on May 27, 2004, which is incorporated herein by reference.

In some embodiments, an embolic coil that is formed of a wound ribbon, such as embolic coil 10, can have a relatively high density of radiopaque material (e.g., relative to conventional embolic coils). This can cause the embolic coil to have a relatively high radiopacity, which can be advantageous because as the radiopacity of an embolic coil increases, the visibility of the embolic coil under X-ray fluoroscopy can also increase.

Figure 1D:
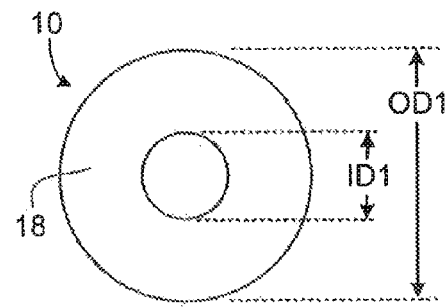
FIG. 1D is a cross-sectional view of the embolic coil of FIG A, taken along line 1D-1D.

As shown in FIGS. 1C and 1D, embolic coil 10 in its primary shape has an inner diameter ID1 and an outer diameter OD1. In some embodiments, inner diameter ID1 is at least 0.001 inch (e.g., at least 0.002 inch, at least 0.004 inch, at least 0.005 inch, at least 0.01 inch, at least 0.015 inch, at least 0.02 inch, at least 0.025 inch, at least 0.03 inch, at least 0.035 inch) and/or at most 0.036 inch (e.g., at most 0.035 inch, at most 0.03 inch, at most 0.025 inch, at most 0.02 inch, at most 0.015 inch, at most 0.01 inch, at most 0.005 inch, at most 0.004 inch, at most 0.002 inch). In certain embodiments, outer diameter OD1 is at least 0.003 inch (e.g., at least 0.005 inch, at least 0.01 inch, at least 0.012 inch, at least 0.015 inch, at least 0.02 inch, at least 0.03 inch, at least 0.035 inch) and/or at most 0.038 inch (e.g., at most 0.035 inch, at most 0.03 inch, at most 0.02 inch, at most 0.015 inch, at most 0.012 inch, at most 0.01 inch, at most 0.005 inch).

As shown in FIG. 1C, embolic coil 10 in its primary shape has a length L2. In some embodiments, length L2 can be at least about 0.2 centimeter (e.g., at least about 0.5 centimeter, at least about one centimeter, at least about five centimeters, at least about 10 centimeters, at least about 15 centimeters, at least about 20 centimeters, at least about 30 centimeters), and/or at most about 40 centimeters (e.g., at most about 30 centimeters, at most about 20 centimeters, at most about 15 centimeters, at most about 10 centimeters, at most about five centimeters, at most about one centimeter, at most about 0.5 centimeter).

The pitch of an embolic coil is the sum of the thickness of one winding of ribbon (e.g., winding 12 of ribbon 18) and the amount of space between that winding and a consecutive winding of ribbon (e.g., winding 14 of ribbon 18). FIG. 1B shows the pitch P1 of embolic coil 10. Because the windings of embolic coil 10 are flush with each other, pitch P1 of embolic coil 10 is equal to the thickness of a winding of embolic coil 10, such as thickness T3 of winding 12 (FIG.

1A). The thickness of a winding of embolic coil 10 is, in turn, equal to width W1 of the rectangular transverse cross-section of ribbon 18. In some embodiments, pitch P1 can be at most 0.005 inch (e.g., at most 0.0045 inch, at most 0.004 inch, at most 0.003 inch, at most 0.002 inch, at most 0.0015 inch, at most 0.001 inch), and/or at least 0.0005 inch (e.g., at least 0.001 inch, at least 0.0015 inch, at least 0.002 inch, at least 0.003 inch, at least 0.004 inch, at least 0.0045 inch).

Figure 2:
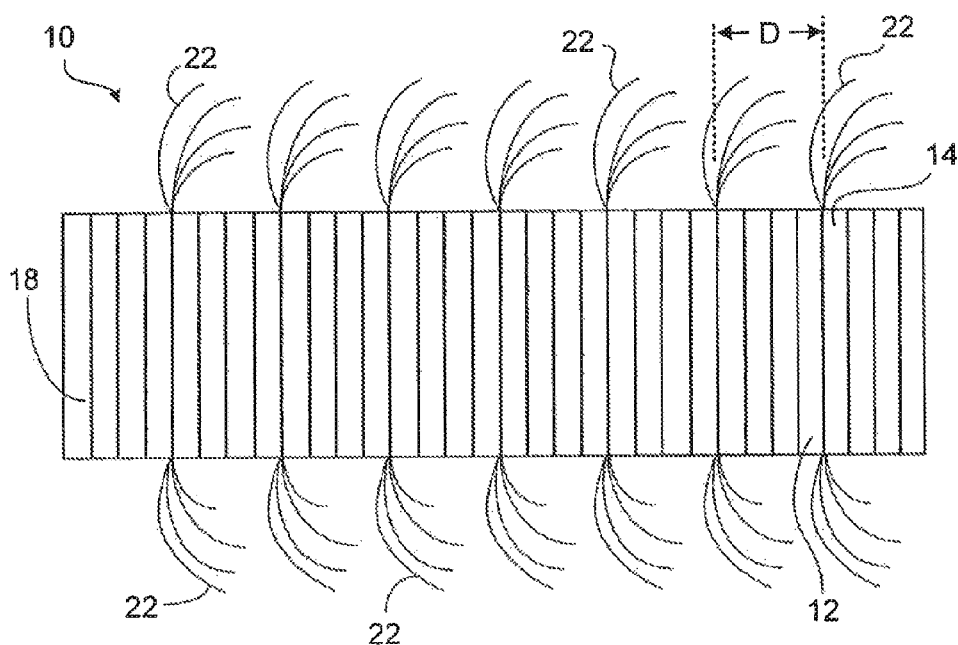
FIG. 2 is a side view of an embodiment of an embolic coil.

In certain embodiments, embolic coil 10 can further include fibers. For example, FIG. 2 shows embolic coil 10 with fibers 22 tightly fitted between consecutive windings, such as windings 12 and 14. The substantial contact between consecutive windings of ribbon 18 may enhance the ability of embolic coil 10 to retain fibers 22. In some embodiments, the distance D between the location of one bunch of fibers 22 and the location of the next bunch of fibers 22 on embolic coil 10 can be at least about two millimeters (e.g., at least about four millimeters, at least about six millimeters, at least about eight millimeters), and/or at most about nine millimeters (e.g., at most about eight millimeters, at most about six millimeters, at most about four millimeters). While FIG. 2 shows bunches of fibers that are all separated from their neighboring bunches of fibers by the same number of windings, in some embodiments, an embolic coil may have a different configuration of fibers. For example, in certain embodiments, an embolic coil may have only one bunch of fibers, or may have bunches of fibers that are separated from their neighboring bunches of fibers by different numbers of windings. As an example, one bunch of fibers on an embolic coil may be separated from a neighboring bunch of fibers by three windings, while another bunch of fibers on the embolic coil is separated from a neighboring bunch of fibers by five windings.

Fibers 22 typically can be made of one or more materials that can enhance thrombosis (e.g., at a target site). In some embodiments, fibers 22 can be made of one or more polyesters and/or polyamides. Examples of materials from which fibers 22 can be made include polyethylene terephthalate (e.g., Dacron®), nylon, and collagen. In certain embodiments, fibers 24 can have a length of from about 0.5 millimeter to about five millimeters (e.g., about 2.5 millimeters).

Embolic coils can generally be used in a number of different applications, such as neurological applications and/or peripheral applications. In some embodiments, embolic coils can be used to embolize a lumen of a subject (e.g., to occlude a vessel), and/or to treat an aneurysm (e.g., an intercranial aneurysm), an arteriovenous malformation (AVM), or a traumatic fistula. In certain embodiments, embolic coils can be used to embolize a tumor (e.g., a liver tumor). In some embodiments, embolic coils can be used in transarterial chemoembolization (TACE).

Figure 3A:
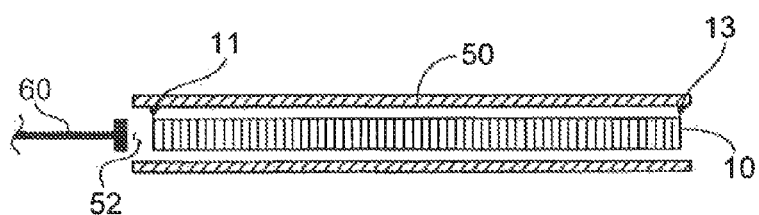
FIGS. 3A-3C illustrate the delivery of an embodiment of an embolic coil to the site of an aneurysm.
Figure 3B:
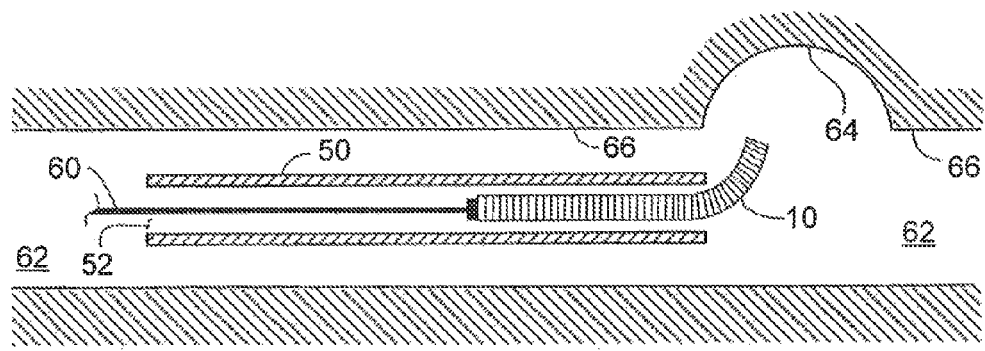
Figure 3C:
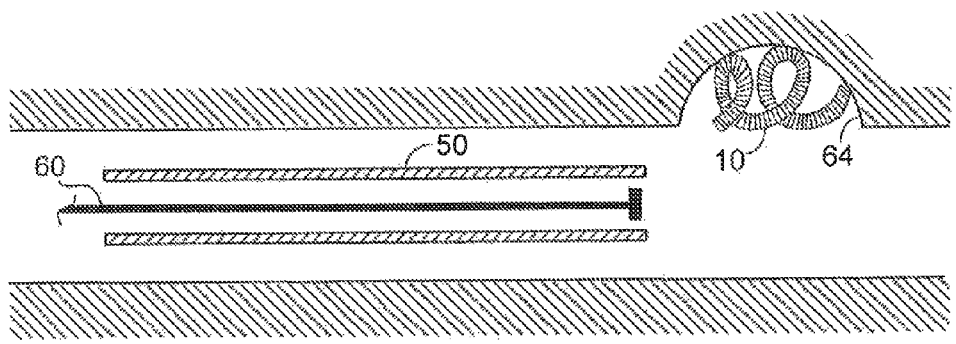

FIGS. 3A-3C show the use of embolic coil 10 to fill and occlude an aneurysmal sac. FIG. 3A shows embolic coil 10, loaded into a lumen 52 of a catheter 50, and a pusher wire 60 disposed outside of catheter 50. In some embodiments in which embolic coil 10 has an outer diameter OD1 of 0.018 inch, catheter 50 can have an inner diameter of 0.021 inch. An example of a catheter having an inner diameter of 0.021 inch is the Renegade® 18 Microcatheter (from Boston Scientific Corp.).

As shown in FIG. 3A, embolic coil 10 includes a proximal end 11 and a distal end 13. Neither proximal end 11 nor distal end 13 is attached to anything. For example, neither proximal end 11 nor distal end 13 is attached to a medical device (e.g., a catheter) or a medical device component (e.g., a guidewire). In some embodiments, embolic coil 10 can be disposed within a carrier fluid (e.g., a saline solution, a contrast agent, a heparin solution) while embolic coil 10 is within lumen 52 of catheter 50. In FIG. 3B, catheter 50 is delivered into a lumen 62 of a subject, and pusher wire 60 is inserted into lumen 52 of catheter 50, such that pusher wire 60 contacts embolic coil 10. Pusher wire 60 is then used to push embolic coil 10 out of catheter 50, into lumen 62, and toward an aneurysmal sac 64 formed in a wall 66 of lumen 62. FIG. 3C shows embolic coil 10 filling aneurysmal sac 64 after embolic coil 10 has been pushed out of catheter 50 by pusher wire 60. By filling aneurysmal sac 64, embolic coil 10 helps to occlude aneurysmal sac 64. In some embodiments in which embolic coil 10 includes fibers (e.g., fibers 22), this occlusion of aneurysmal sac 64 can be accelerated by the fibers, which can enhance thrombosis within aneurysmal sac 64. An accelerated embolization procedure can benefit the subject by, for example, reducing exposure time to fluoroscopy.

Generally, the design of embolic coil 10 (e.g., the substantial contact between consecutive windings of ribbon 18) can result in embolic coil 10 having a relatively high effective column strength. The effective column strength of embolic coil 10 is the column strength (the compression load at which embolic coil 10 will buckle) of embolic coil 10 when embolic coil 10 is constrained within lumen 52 of catheter 50. Because embolic coil 10 can have a relatively high effective column strength, embolic coil 10 can also have good pushability. As a result, in some embodiments in which embolic coil 10 includes fibers 22, even if fibers 22 adhere to the walls of lumen 52, embolic coil 10 can be sufficiently pushable to overcome the adhesion.

In general, embolic coil 10 has a primary shape and a secondary shape. Embolic coil 10 exhibits only its primary shape when embolic coil 10 is extended within lumen 52 of catheter 50 (as shown in FIG. 3A). As embolic coil 10 exits catheter 50, however, embolic coil 10 further assumes its secondary shape, which allows embolic coil 10 to fill aneurysmal sac 64. Typically, the primary shape of embolic coil 10 can be selected for deliverability, and the secondary shape of embolic coil 10 can be selected for application (e.g., embolization of an aneurysm).

As FIGS. 4-10 illustrate, an embolic coil can have any of a number of different secondary shapes, which can depend on the particular application for the embolic coil.

Figures 4, 5:
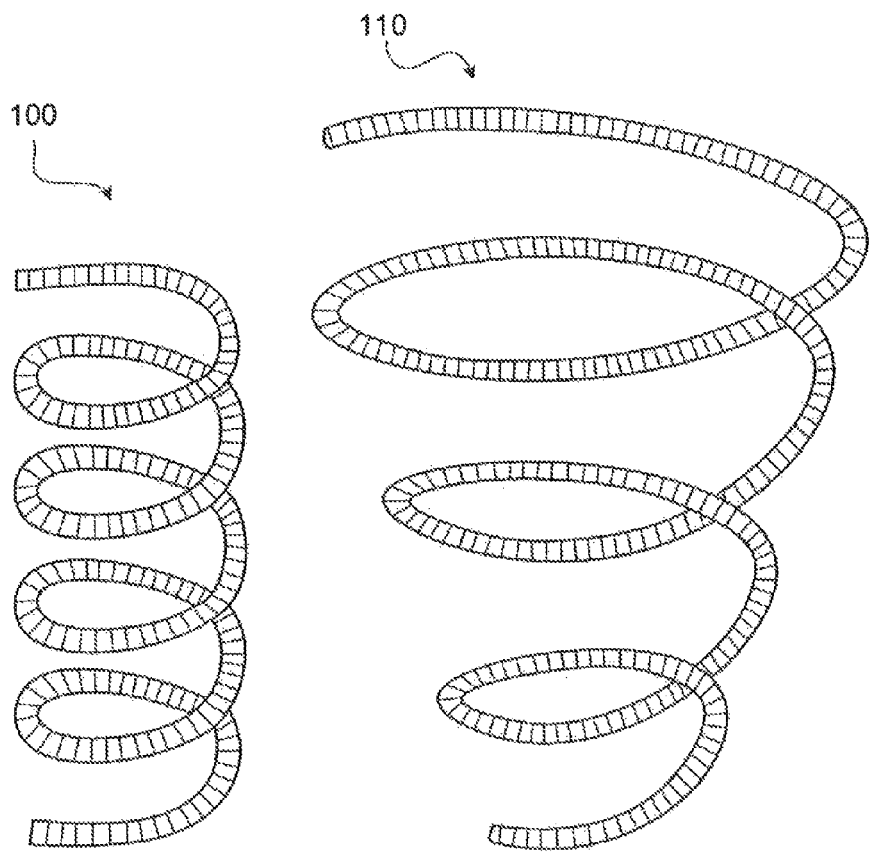
FIG. 4 is a perspective view of an embodiment of an embolic coil.
FIG. 5 is a perspective view of an embodiment of an embolic coil.

For example, FIG. 4 shows an embolic coil 100 with a spiral secondary shape, which can be used, for example, to provide a supportive framework along a vessel wall. Alternatively or additionally, an embolic coil with a spiral secondary shape can be used to hold other embolic coils that are subsequently delivered to the target site.

FIG. 5 shows an embolic coil 110 with a single apex vortex secondary shape, which can be used, for example, to close the center of a target site (e.g., a vessel, an aneurysm) that is to be occluded, and/or to occlude a target site in conjunction with an embolic coil such as embolic coil 100 (FIG. 4). An embolic coil with a single apex vortex secondary shape can be used to occlude a vessel having low flow, intermediate flow, or high flow. In some embodiments, multiple embolic coils with single apex vortex secondary shapes can be used to occlude a vessel. In certain embodiments, an embolic coil with a single apex vortex secondary shape can be used as a packing coil, such that the coil can be packed into a vessel that is slightly smaller than the diameter of the coil. As an example, a six-millimeter diameter coil can be packed into a vessel having a five-millimeter diameter. In some embodiments, an embolic coil with a single apex vortex secondary shape can be used to embolize a tumor and/or to treat gastrointestinal bleeding.

Figure 6:
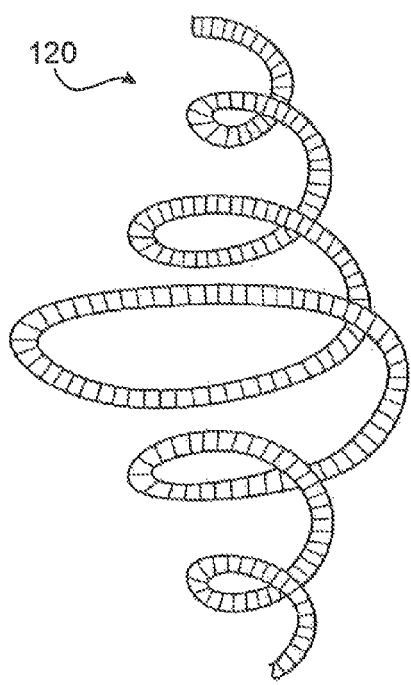
FIG. 6 is a perspective view of an embodiment of an embolic coil.

As shown in FIG. 6, an embolic coil 120 can have a dual apex vortex secondary shape (also known as a diamond secondary shape), which, like the single apex vortex secondary shape, can used, for example, to close the center of a target site (e.g., a vessel, an aneurysm) that is to be occluded, and/or to occlude a target site in conjunction with an embolic coil such as embolic coil 100 (FIG. 4). An embolic coil with a dual apex vortex secondary shape can be used to occlude a vessel having low flow, intermediate flow, or high flow, and can be used alone or in combination with other embolic coils (e.g., other embolic coils having dual apex vortex secondary shapes). In certain embodiments, an embolic coil with a dual apex vortex secondary shape can be used as a packing coil. In some embodiments, an embolic coil with a dual apex vortex secondary shape can be used to embolize a tumor and/or to treat gastrointestinal bleeding.

Figure 7:
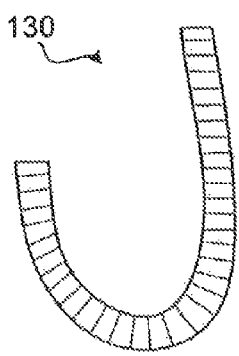
FIG. 7 is a perspective view of an embodiment of an embolic coil.

FIG. 7 shows an embolic coil 130 with a secondary shape in the form of a J, which can be used, for example, to fill remaining space in an aneurysm that was not filled by other coils. In some embodiments, an operator (e.g., a physician) can hook the curved portion of embolic coil 130 into a coil or coil mass that has already been deployed at a target site, and then shape the straighter portion of coil 130 to fill the target site.

Figure 8A:
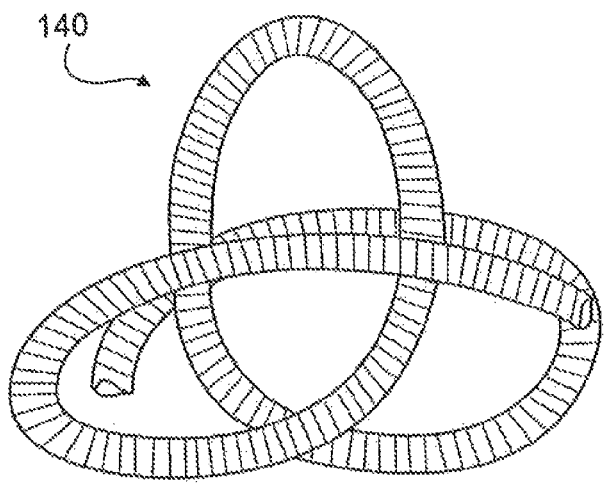
FIG. 8A is a front view of an embodiment of an embolic coil.
Figure 8B:
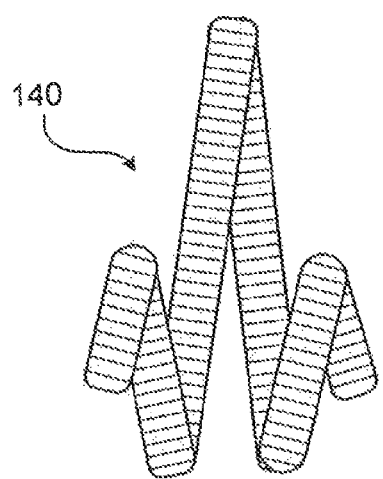
FIG. 8B is a side view of the embolic coil of FIG. 8A.

FIGS. 8A and 8B show an embolic coil 140 having a complex helical secondary shape. An embolic coil with a complex helical secondary shape can be used, for example, to frame a target site. In certain embodiments, an embolic coil with a complex helical secondary shape can be used as an anchoring coil that helps to hold other embolic coils in place at a target site (e.g., thereby allowing additional embolic coils to be packed into the target site).

Figure 9A:
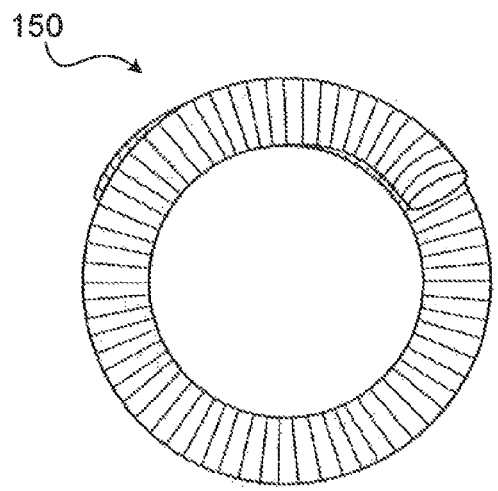
FIG. 9A is a front view of an embodiment of an embolic coil.
Figure 9B:
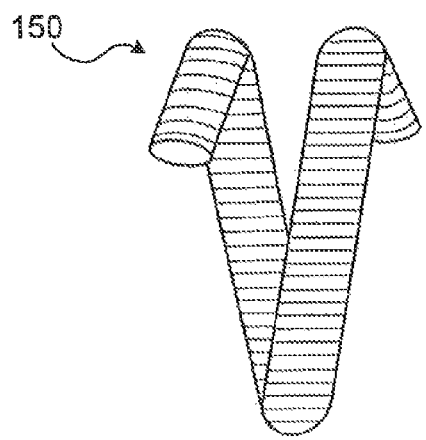
FIG. 9B is a side view of the embolic coil of FIG. 9A.

FIGS. 9A and 9B show an embolic coil 150 having a helical secondary shape. An embolic coil with a helical secondary shape can be used, for example, as a packing coil.

Figure 10:
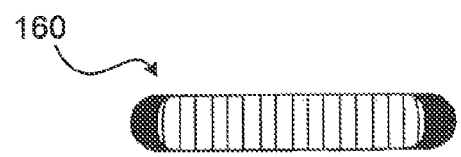
FIG. 10 is a side view of an embodiment of an embolic coil.

FIG. 10 shows an embolic coil 160 having a straight secondary shape. An embolic coil with a straight secondary shape can be used, for example, in a relatively small vessel (e.g., to block blood flow to a tumor).

In some embodiments, an embolic coil (e.g., embolic coil 10) can be relatively flexible. For example, in certain embodiments, the stiffness of an embolic coil can be at most about 0.01 pound-force (e.g., at most about 0.004 pound-force), and/or at least about 0.001 pound-force (e.g., at least about 0.004 pound-force). Coil stiffness is determined by measuring the force required to compress the largest outer diameter of a secondary shape of a coil by five percent. A dynamic testing machine is used to measure coil stiffness as follows. The region of a secondary coil having the largest outer diameter is cut away from the secondary coil and placed in the gripping mechanism of the testing machine, such that only half of the largest outer diameter of the secondary coil (a semicircle shape) is exposed. The sample is placed directly below an anvil-like fixture that compresses down on the surface of the outer diameter. The force required to compress the sample by five percent of the largest outer diameter of the secondary shape of the coil is then measured.

Figure 11A:
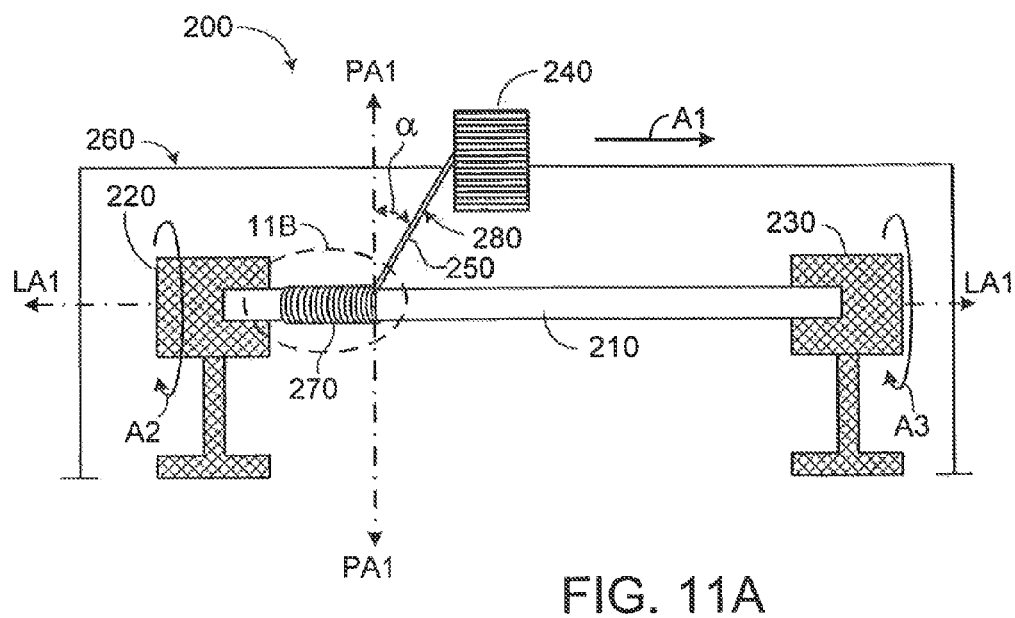
FIG. 11A is a side view of an embodiment of a process for forming an embolic coil.
Figure 11B:
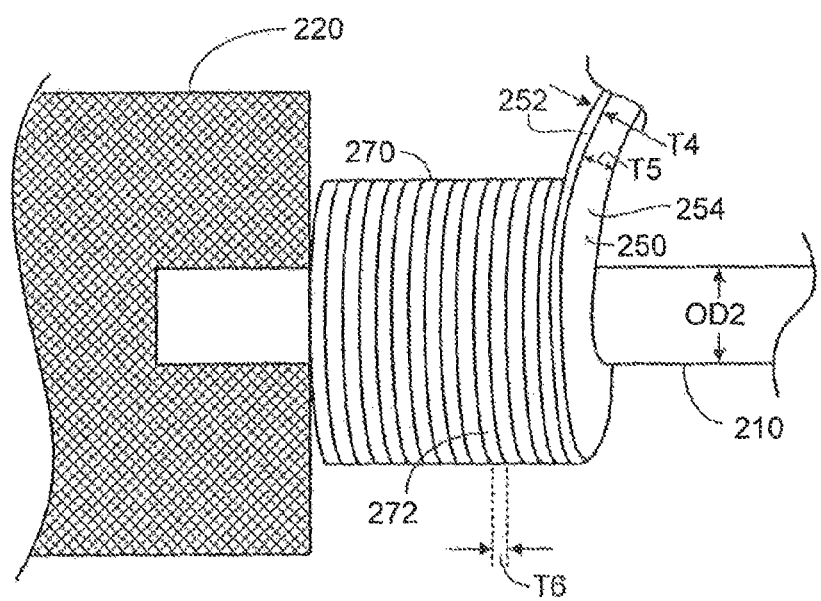
FIG. 11B is an enlarged view of region 11B in FIG. 1A.
Figure 12A:
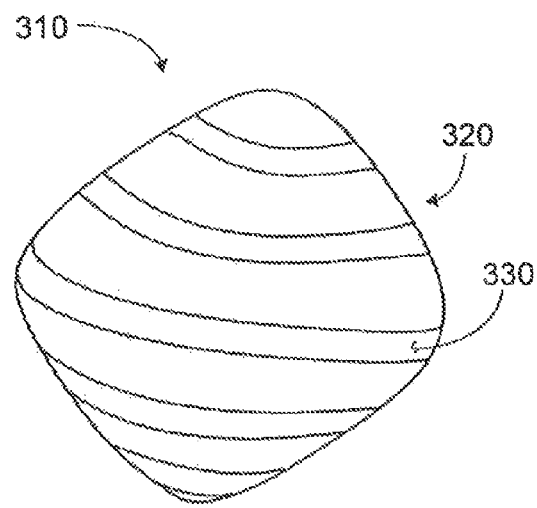
FIG. 12A is a side view of an embodiment of a mandrel.
Figure 12B:
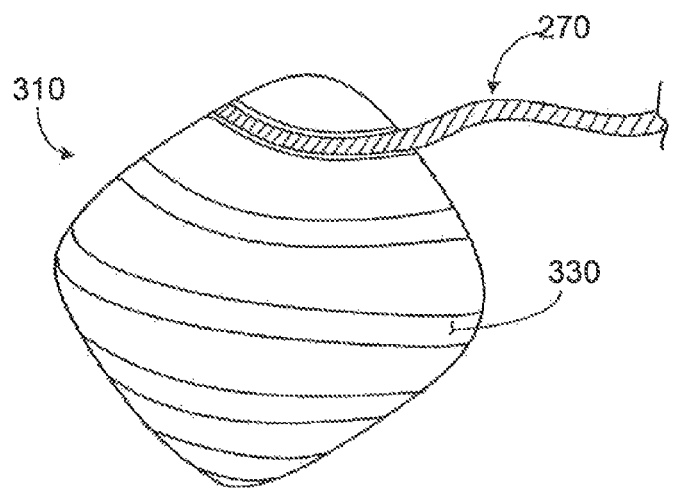
FIGS. 12B and 12C are illustrations of an embodiment of a process for forming an embolic coil using the mandrel of FIG. 12A.
Figure 12C:
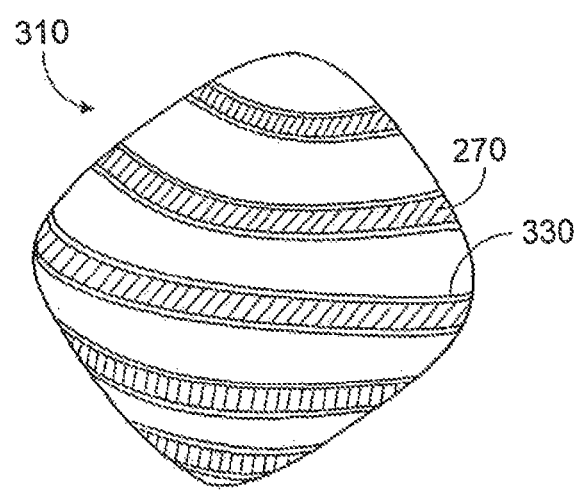

FIGS. 1A and 11B illustrate a process for forming an embolic coil (e.g., embolic coil 10) in its primary shape, and FIGS. 12A-12C show a process for forming the secondary shape of the embolic coil.

As shown in FIG. 11A, a coil-forming apparatus 200 includes a mandrel 210 held by two rotatable chucks 220 and 230. A spool 240 of ribbon 250 is disposed above mandrel 210, and is attached to a linear drive 260. To form an embolic coil in its primary shape, chucks 220 and 230 are activated so that they rotate in the direction of arrows A2 and A3, thereby rotating mandrel 210. Linear drive 260 also is activated, and moves spool 240 in the direction of arrow A1. The rotation of mandrel 210 pulls ribbon 250 from spool 240 at a predetermined pull-off angle, and causes ribbon 250 to wrap around mandrel 210, forming a coil 270.

As shown in FIG. 11B, ribbon 250 has a side 252 having a relatively small thickness T4 and a side 254 having a relatively large thickness T5. In forming coil 270, ribbon 250 is wound around mandrel 210 on edge, so that the thickness T6 of each winding (e.g., winding 272) of coil 270 is equal to thickness T4 of side 252. The winding of ribbon 250 on edge to form coil 270 can cause the windings of coil 270 to have a relatively high degree of contact with each other.

As FIG. 1A shows, the pull-off angle (a) is the angle between axis PA1, which is perpendicular to longitudinal axis LA1 of mandrel 210, and the portion 280 of ribbon 250 between spool 240 and coil 270. In some embodiments, a can be from about one degree to about six degrees (e.g., from about 1.5 degrees to about five degrees, from about 1.5 degrees to about 2.5 degrees, about two degrees). In certain embodiments, a controller (e.g., a programmable logic controller) can be used to maintain the pull-off angle in coil-forming apparatus 200. Because mandrel 210 is rotating as it is pulling ribbon 250 from spool 240, and because linear drive 260 is moving spool 240 in the direction of arrow A1, ribbon 250 forms coil 270 in a primary shape around mandrel 210. Coil 270 can be formed, for example, at room temperature (25° C.).

After coil 270 has been formed, chucks 220 and 230, and linear drive 260, are deactivated, and portion 280 of ribbon 250 is cut. Mandrel 210 is then released from chuck 220, and coil 270 is pulled off of mandrel 210. While coil 270 might lose some of its primary shape as it is pulled off of mandrel 210, coil 270 can generally return to its primary shape shortly thereafter, because of memory imparted to coil 270 during formation. In some embodiments, after coil 270 has been removed from mandrel 210, one or both of the ends of coil 270 can be heated and melted to form rounder, more biocompatible (e.g., atraumatic) ends.

Mandrel 210 can be formed of, for example, a metal or a metal alloy, such as stainless steel. In some embodiments, mandrel 210 can be formed of one or more polymers, such as Teflon® (polytetrafluoroethylene) or Delrin® (polyoxymethylene). In certain embodiments, mandrel 210 can be formed of a shape-memory material, such as Nitinol.

Mandrel 210 has an outer diameter OD2 (FIG. 11B). In some embodiments, outer diameter OD2 can be at least 0.0005 inch (e.g., at least 0.001 inch, at least 0.004 inch, at least 0.005 inch, at least 0.01 inch, at least 0.015 inch, at least 0.02 inch, at least 0.025 inch) and/or at most 0.03 inch (e.g., at most 0.025 inch, at most 0.02 inch, at most 0.015 inch, at most 0.01 inch, at most 0.005 inch, at most 0.004 inch, at most 0.001 inch).

The tension of mandrel 210 as it is held between chucks 220 and 230 preferably is sufficiently high to avoid vibration of mandrel 210 during the winding process, and sufficiently low to avoid stretching of mandrel 210 during the winding process. In some instances, significant stretching of mandrel 210 during the winding process could cause coil 270 to have a smaller primary shape than desired, and/or could make it relatively difficult to remove coil 270 from mandrel 210. In certain embodiments, the tension of mandrel 210 can be from about 100 grams to about 1,000 grams (e.g., from about 300 grams to about 600 grams, from about 400 grams to about 500 grams). For example, the tension of mandrel 210 can be about 506 grams.

In some embodiments, ribbon 250 can be wound around mandrel 210 at a tension of at least about four grams (e.g., at least about five grams, at least about six grams, at least about 10 grams, at least about 22 grams, at least about 27 grams, at least about 32 grams, at least about 40 grams, at least about 60 grams, at least about 65 grams, at least about 85 grams) and/or at most about 100 grams (e.g., at most about 85 grams, at most about 65 grams, at most about 60 grams, at most about 40 grams, at most about 32 grams, at most about 27 grams, at most about 22 grams, at most about 10 grams, at most about six grams, at most about five grams).

In certain embodiments, the length of coil 270 in its primary shape and while under tension on mandrel 210 can be from about 10 centimeters to about 250 centimeters (e.g., from about 50 centimeters to about 200 centimeters, from about 130 centimeters to about 170 centimeters, from about 144 centimeters to about 153 centimeters, from about 147 centimeters to about 153 centimeters). For example, the length of coil 270 in its primary shape and while under tension on mandrel 210 can be about 132 centimeters or about 147 centimeters. Coil 270 may recoil to some extent (e.g., by at most about five centimeters) when portion 280 of ribbon 250 is severed, such that coil 270 will be somewhat smaller once it has been removed from mandrel 210. In some embodiments, coil 270 can have a length of from about five centimeters to about 225 centimeters (e.g., from about 25 centimeters to about 170 centimeters, from about 120 centimeters to about 140 centimeters, from about 137 centimeters to about 140 centimeters) after being removed from mandrel 210. After coil 270 has been removed from mandrel 210, coil 270 can be cut into smaller coils.

Once coil 270 has been formed in its primary shape, coil 270 can be further shaped into a secondary shape, as shown in FIGS. 12A-12C.

FIG. 12A shows a mandrel 310 used to form the secondary shape of coil 270. While mandrel 310 is shaped to form a diamond, other types of mandrels can be used to form other secondary shapes. Mandrel 310 is formed of a diamond-shaped block 320 with grooves 330 cut into its surface. As shown in FIGS. 12B and 12C, coil 270 in its primary shape is wrapped around mandrel 310, such that coil 270 fills grooves 330, creating the secondary shape. The ends of coil 270 are then attached (e.g., pinned) to mandrel 310, and coil 270 is heat-treated to impart memory to coil 270. In some embodiments, coil 270 can be heat-treated at a temperature of at least about 1000° C. (e.g., at least about 1050° C., at least about 1100° C., at least about 1150° C.), and/or at most about 1200° C. (e.g., at most about 1150° C., at most about 1100° C., at most about 1050° C.). In certain embodiments, the heat treatment of coil 270 can last for a period of from about 10 minutes to about 40 minutes (e.g., about 25 minutes). After being heat-treated, coil 270 is unwrapped from mandrel 310. The removal of coil 270 from mandrel 310 allows coil 270 to reassume its secondary shape. In some embodiments, after coil 270 has been removed from mandrel 310, one or both of the ends of coil 270 can be heated and melted to form rounder, more biocompatible (e.g., atraumatic) ends.

Mandrel 310 can be formed of, for example, a metal or a metal alloy (e.g., stainless steel). In some embodiments, mandrel 310 can be formed of a plated metal or a plated metal alloy (e.g., chrome-plated stainless steel).

After coil 270 has been removed from mandrel 310, fibers can be attached to coil 270. In some embodiments, coil 270 can be stretched prior to attaching the fibers, so that coil 270 is in its extended primary shape, and can then be loaded onto a fibering mandrel (e.g., a fibering mandrel from Sematool Mold and Die Co., Santa Clara, Calif.). In certain embodiments, fibers can be snapped in between windings of coil 270. In some embodiments, fibers can be tied to windings of coil 270 and/or wrapped around windings of coil 270. In certain embodiments, fibers can be bonded (e.g., adhesive bonded) to ribbon 250 of coil 270. In certain embodiments, one portion (e.g., one end) of a bunch of fibers can be snapped in between windings in one region of coil 270, and another portion (e.g., the other end) of the same bunch of fibers can be wrapped around part of coil 270 and snapped in between windings in another region of coil 270.

Embolic coils and methods of making embolic coils are described, for example, in Elliott et al., U.S. patent application Ser. No. 11/000,741, filed on Dec. 1, 2004, and entitled "Embolic Coils", which is incorporated herein by reference.

In some embodiments, an embolic coil such as embolic coil 10 can include one or more therapeutic agents (e.g., drugs). For example, ribbon 18 and/or fibers 22 can include one or more therapeutic agents (e.g., dispersed within and/or encapsulated by the material of ribbon 18 and/or fibers 22), and/or can be coated with one or more coatings including one or more therapeutic agents. In some embodiments, the therapeutic agents can be dispersed within, and/or encapsulated by, the coatings. Embolic coil 10 can, for example, be used to deliver the therapeutic agents to a target site.

In certain embodiments, one component of embolic coil 10 (e.g., a coating on ribbon 18) can include one or more therapeutic agents that are the same as, or different from, one or more therapeutic agents in another component of embolic coil 10 (e.g., a coating on fibers 22). In certain embodiments in which ribbon 18 and/or fibers 22 are coated by coatings including one or more therapeutic agents, the coatings can include one or more bioerodible and/or bioabsorbable materials. When the coatings are eroded and/or absorbed, they can release the therapeutic agents into the body of the subject (e.g., during delivery and/or at a target site).

In some embodiments, embolic coil 10 can include one or more therapeutic agents that are coated onto ribbon 18, fibers 22, and/or one or more coatings on ribbon 18 and/or fibers 22. In certain embodiments, a therapeutic agent can be compounded with a polymer that is included in a coating on ribbon 18 and/or fibers 22. In some embodiments, a therapeutic agent can be applied to the surface of embolic coil 10 by exposing embolic coil 10 to a high concentration solution of the therapeutic agent.

In some embodiments, a therapeutic agent-coated embolic coil can include a coating (e.g., a bioerodible and/or bioabsorbable polymer coating) over the surface of the therapeutic agent. The coating can assist in controlling the rate at which therapeutic agent is released from the embolic coil. For example, the coating can be in the form of a porous membrane. The coating can delay an initial burst of therapeutic agent release. The coating can be applied by dipping or spraying the embolic coil. The coating can include therapeutic agent or can be substantially free of therapeutic agent. The therapeutic agent in the coating can be the same as or different from a therapeutic agent on a surface layer of the embolic coil and/or within the embolic coil (e.g., within a ribbon forming the embolic coil). A polymer coating (e.g., that is bioerodible and/or bioabsorbable) can be applied to an embolic coil surface and/or to a coated embolic coil surface in embodiments in which a high concentration of therapeutic agent has not been applied to the embolic coil surface or to the coated embolic coil surface.

Coatings are described, for example, in Buiser et al., U.S. patent application Ser. No. 11/311,617, filed on Dec. 19, 2005, and entitled "Coils", and in DiMatteo et al., U.S. Patent Application Publication No. US 2004/0076582 A1, published on Apr. 22, 2004, and entitled "Agent Delivery Particle", both of which are incorporated herein by reference.

In some embodiments, one or more embolic coils can be disposed in a therapeutic agent that can serve as a pharmaceutically acceptable carrier.

Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; gene therapies; nucleic acids with and without carrier vectors (e.g., recombinant nucleic acids, DNA (e.g., naked DNA), cDNA, RNA, genomic DNA, cDNA or RNA in a non-infectious vector or in a viral vector which may have attached peptide targeting sequences, antisense nucleic acids (RNA, DNA)); peptides (e.g., growth factor peptides, such as basic fibroblast growth factor (bFGF)); oligonucleotides; gene/vector systems (e.g., anything that allows for the uptake and expression of nucleic acids); DNA chimeras (e.g., DNA chimeras which include gene sequences and encoding for ferry proteins such as membrane translocating sequences ("MTS") and herpes simplex virus-1 ("VP22")); compacting agents (e.g., DNA compacting agents); viruses; polymers; hyaluronic acid; proteins (e.g., enzymes such as ribozymes, asparaginase); immunologic species; nonsteroidal anti-inflammatory medications; chemoagents; pain management therapeutics; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); calcium entry blockers; and survival genes which protect against cell death (e.g., anti-apoptotic Bcl-2 family factors and Akt kinase).

Exemplary non-genetic therapeutic agents include: antithrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, acetyl salicylic acid, sulfasalazine and mesalamine; antineoplastic/antiproliferative/anti-mitotic agents such as paclitaxel, 5-fluorouracil, cisplatin, methotrexate, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, antithrombin compounds, platelet receptor antagonists, antithrombin antibodies, anti-platelet receptor antibodies, aspirin, prostaglandin inhibitors, platelet inhibitors and tick antiplatelet factors or peptides; vascular cell growth promoters such as growth factors, transcriptional activators, and translational promoters; vascular cell growth inhibitors such as growth factor inhibitors (e.g., PDGF inhibitor-Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with, endogenous vasoactive mechanisms.

Exemplary genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP 1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them. Vectors of interest for delivery of genetic therapeutic agents include: plasmids; viral vectors such as adenovirus (AV), adenoassociated virus (AAV) and lentivirus; and non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents appropriate for the practice of the present invention are disclosed in Kunz et al., U.S. Pat. No. 5,733,925, assigned to NeoRx Corporation, which is incorporated herein by reference. Therapeutic agents disclosed in this patent include the following:

"Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

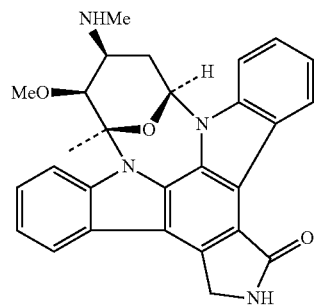 [SMILES: CN[C@H]1C[C@H]2O[C@@](C)([C@H]1OC)n1c3ccccc3c3c4c(c5c6ccccc6n2c5c31)C(=O)NC4]

as well as diindoloalkaloids having one of the following general structures:

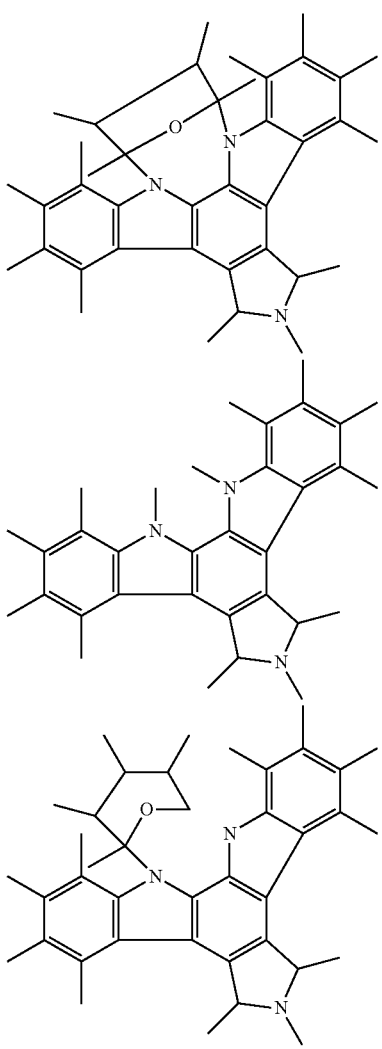

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or 12.

Agents that inhibit the intracellular increase in cell volume (i.e., the tissue volume occupied by a cell), such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, *Pseudomonas* exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, *Pseudomonas* exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents include one or more of the following: calcium-channel blockers, including benzothiazapines (e.g., diltiazem, clentiazem); dihydropyridines (e.g., nifedipine, amlodipine, nicardapine); phenylalkylamines (e.g., verapamil); serotonin pathway modulators, including 5-HT antagonists (e.g., ketanserin, naftidrofuryl) and 5-HT uptake inhibitors (e.g., fluoxetine); cyclic nucleotide pathway agents, including phosphodiesterase inhibitors (e.g., cilostazole, dipyridamole), adenylate/guanylate cyclase stimulants (e.g., forskolin), and adenosine analogs; catecholamine modulators, including α-antagonists (e.g., prazosin, bunazosine), β-antagonists (e.g., propranolol), and α/β-antagonists (e.g., labetalol, carvedilol); endothelin receptor antagonists; nitric oxide donors/releasing molecules, including organic nitrates/nitrites (e.g., nitroglycerin, isosorbide dinitrate, amyl nitrite), inorganic nitroso compounds (e.g., sodium nitroprusside), sydnonimines (e.g., molsidomine, linsidomine), nonoates (e.g., diazenium diolates, NO adducts of alkanediamines), S-nitroso compounds, including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), C-nitroso-, O-nitroso- and N-nitroso-compounds, and Larginine; ACE inhibitors (e.g., cilazapril, fosinopril, enalapril); ATII-receptor antagonists (e.g., saralasin, losartin); platelet adhesion inhibitors (e.g., albumin, polyethylene oxide); platelet aggregation inhibitors, including aspirin and thienopyridine (ticlopidine, clopidogrel) and GP IIb/IIIa inhibitors (e.g., abciximab, epitifibatide, tirofiban, intergrilin); coagulation pathway modulators, including heparinoids (e.g., heparin, low molecular weight heparin, dextran sulfate, β-cyclodextrin tetradecasulfate), thrombin inhibitors (e.g., hirudin, hirulog, PPACK (D-phe-L-propyl-L-arg-chloromethylketone), argatroban), FXa inhibitors (e.g., antistatin, TAP (tick anticoagulant peptide)), vitamin K inhibitors (e.g., warfarin), and activated protein C; cyclooxygenase pathway inhibitors (e.g., aspirin, ibuprofen, flurbiprofen, indomethacin, sulfinpyrazone); natural and synthetic corticosteroids (e.g., dexamethasone, prednisolone, methprednisolone, hydrocortisone); lipoxygenase pathway inhibitors (e.g., nordihydroguairetic acid, caffeic acid; leukotriene receptor antagonists; antagonists of E- and P-selectins; inhibitors of VCAM-1 and ICAM-1 interactions; prostaglandins and analogs thereof, including prostaglandins such as PGE1 and PGI2; prostacyclin analogs (e.g., ciprostene, epoprostenol, carbacyclin, iloprost, beraprost); macrophage activation preventers (e.g., bisphosphonates); HMG-CoA reductase inhibitors (e.g., lovastatin, pravastatin, fluvastatin, simvastatin, cerivastatin); fish oils and omega-3-fatty acids; free-radical scavengers/antioxidants (e.g., probucol, vitamins C and E, ebselen, retinoic acid (e.g., trans-retinoic acid), SOD mimics); agents affecting various growth factors including FGF pathway agents (e.g., bFGF antibodies, chimeric fusion proteins), PDGF receptor antagonists (e.g., trapidil), IGF pathway agents (e.g., somatostatin analogs such as angiopeptin and ocreotide), TGF-β pathway agents such as polyanionic agents (heparin, fucoidin), decorin, and TGF-β antibodies, EGF pathway agents (e.g., EGF antibodies, receptor antagonists, chimeric fusion proteins), TNF-a pathway agents (e.g., thalidomide and analogs thereof), thromboxane A2 (TXA2) pathway modulators (e.g., sulotroban, vapiprost, dazoxiben, ridogrel), protein tyrosine kinase inhibitors (e.g., tyrphostin, genistein, and quinoxaline derivatives); MMP pathway inhibitors (e.g., marimastat, ilomastat, metastat), and cell motility inhibitors (e.g., cytochalasin B); antiproliferative/ antineoplastic agents including antimetabolites such as purine analogs (e.g., 6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin, daunomycin, bleomycin, mitomycin, penicillins, cephalosporins, ciprofalxin, vancomycins, aminoglycosides, quinolones, polymyxins, erythromycins, tertacyclines, chloramphenicols, clindamycins, linomycins, sulfonamides, and their homologs, analogs, fragments, derivatives, and pharmaceutical salts), nitrosoureas (e.g., carmustine, lomustine) and cisplatin, agents affecting microtubule dynamics (e.g., vinblastine, vincristine, colchicine, paclitaxel, epothilone), caspase activators, proteasome inhibitors, angiogenesis inhibitors (e.g., endostatin, angiostatin and squalamine), and rapamycin, cerivastatin, flavopiridol and suramin; matrix deposition/organization pathway inhibitors (e.g., halofuginone or other quinazolinone derivatives, tranilast); endothelialization facilitators (e.g., VEGF and RGD peptide); and blood rheology modulators (e.g., pentoxifylline).

Other examples of therapeutic agents include anti-tumor agents, such as docetaxel, alkylating agents (e.g., mechlorethamine, chlorambucil, cyclophosphamide, melphalan, ifosfamide), plant alkaloids (e.g., etoposide), inorganic ions (e.g., cisplatin), biological response modifiers (e.g., interferon), and hormones (e.g., tamoxifen, flutamide), as well as their homologs, analogs, fragments, derivatives, and pharmaceutical salts.

Additional examples of therapeutic agents include organic-soluble therapeutic agents, such as mithramycin, cyclosporine, and plicamycin. Further examples of therapeutic agents include pharmaceutically active compounds, antisense genes, viral, liposomes and cationic polymers (e.g., selected based on the application), biologically active solutes (e.g., heparin), prostaglandins, prostcyclins, L-arginine, nitric oxide (NO) donors (e.g., lisidomine, molsidomine, NO-protein adducts, NO-polysaccharide adducts, polymeric or oligomeric NO adducts or chemical complexes), enoxaparin, Warafin sodium, dicumarol, interferons, chymase inhibitors (e.g., Tranilast), ACE inhibitors (e.g., Enalapril), serotonin antagonists, 5-HT uptake inhibitors, and beta blockers, and other antitumor and/or chemotherapy drugs, such as BiCNU, busulfan, carboplatinum, cisplatinum, cytoxan, DTIC, fludarabine, mitoxantrone, velban, VP-16, herceptin, leustatin, navelbine, rituxan, and taxotere.

Therapeutic agents are described, for example, in Buiser et al., U.S. patent application Ser. No. 11/311,617, filed on Dec. 19, 2005, and entitled "Coils"; DiMatteo et al., U.S. Patent Application Publication No. US 2004/0076582 A1, published on Apr. 22, 2004, and entitled "Agent Delivery Particle"; Pinchuk et al., U.S. Pat. No. 6,545,097; and Schwarz et al., U.S. Pat. No. 6,368,658, all of which are incorporated herein by reference.

While certain embodiments have been described, other embodiments are possible.

Figure 13A:
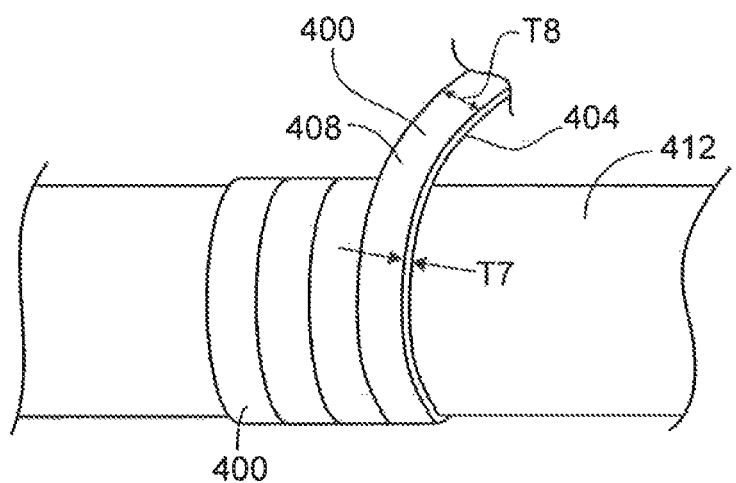
FIG. 13A is an illustration of an embodiment of a process for forming an embolic coil.
Figure 13B:
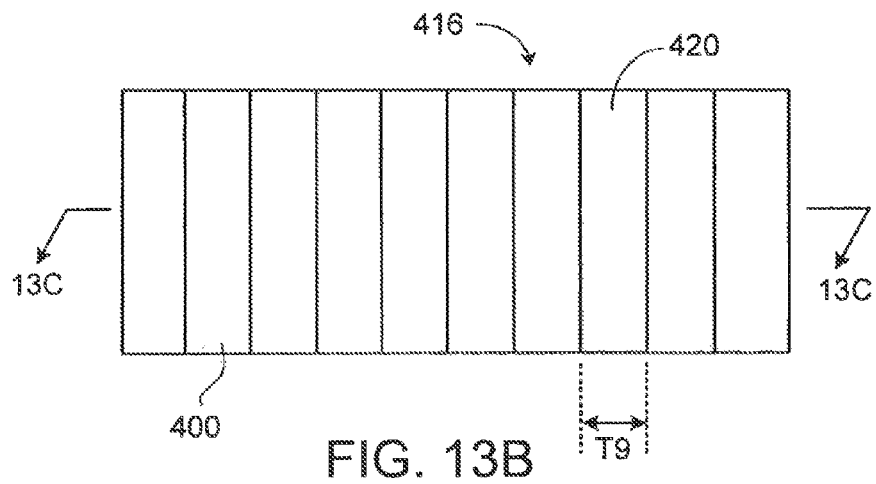
FIG. 13B is a side view of an embodiment of an embolic coil formed using the process of FIG. 13A.
Figure 13C:
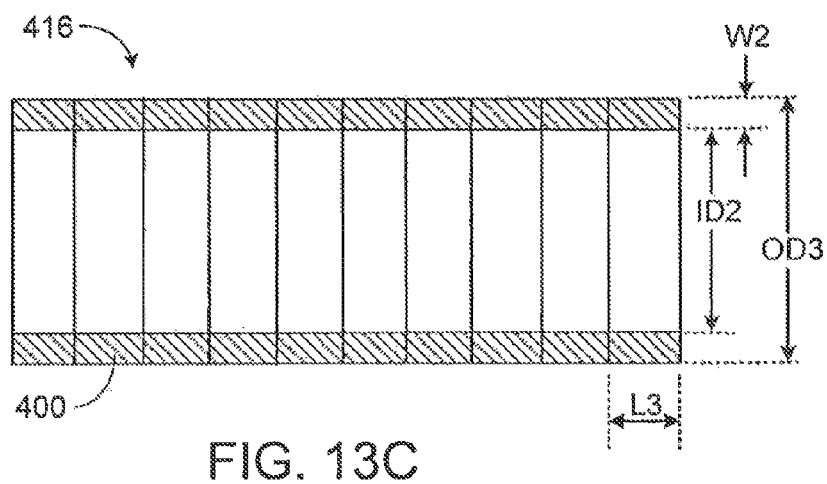
FIG. 13C is a side cross-sectional view of the embolic coil of FIG. 13B, taken along line 13C-13C.

As an example, while the formation of an embolic coil by winding a ribbon on edge has been described, in some embodiments, a different method can be used to form an embolic coil. For example, FIG. 13A shows a ribbon 400 with a side 404 having a relatively small thickness T7 and a side 408 having a relatively large thickness T8. As shown in FIG. 13A, ribbon 400 is wound around a mandrel 412 to form an embolic coil 416 (FIGS. 13B and 13C). Ribbon 400 is not wound on edge, but instead is wound so that the thickness T9 of each winding (e.g., winding 420) of embolic coil 416 is equal to thickness T8 of side 408. As shown in FIG. 13C, ribbon 400 has a rectangular transverse cross-section with a width W2 and a length L3 that is longer than width W2.

Embolic coil 416 has an inner diameter ID2 and an outer diameter OD3. In some embodiments, inner diameter ID2 can be at least 0.001 inch (e.g., at least 0.002 inch, at least 0.004 inch, at least 0.005 inch, at least 0.01 inch, at least 0.015 inch, at least 0.02 inch, at least 0.025 inch, at least 0.03 inch, at least 0.035 inch) and/or at most 0.036 inch (e.g., at most 0.035 inch, at most 0.03 inch, at most 0.025 inch, at most 0.02 inch, at most 0.015 inch, at most 0.01 inch, at most 0.005 inch, at most 0.004 inch, at most 0.002 inch).

In certain embodiments, outer diameter OD3 can be at least 0.003 inch (e.g., at least 0.005 inch, at least 0.01 inch, at least 0.012 inch, at least 0.015 inch, at least 0.02 inch, at least 0.03 inch, at least 0.035 inch) and/or at most 0.038 inch (e.g., at most 0.035 inch, at most 0.03 inch, at most 0.02 inch, at most 0.015 inch, at most 0.012 inch, at most 0.01 inch, at most 0.005 inch).

Figure 14:
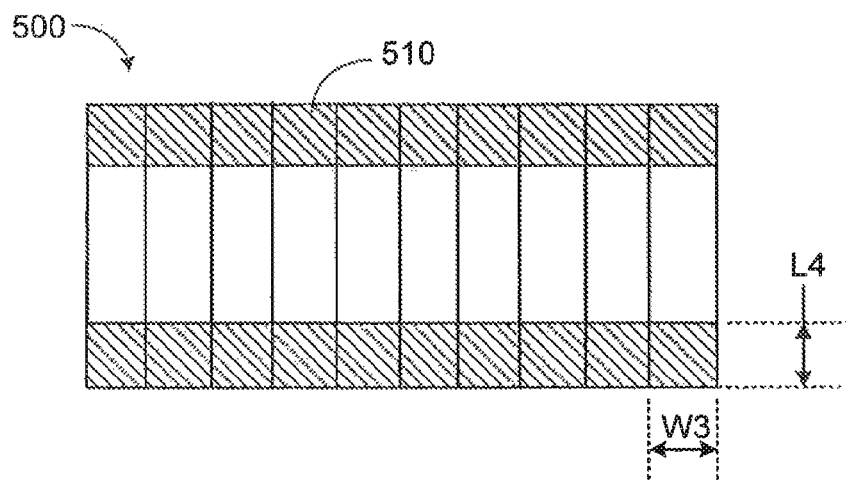
FIG. 14 is a side cross-sectional view of an embodiment of an embolic coil.
Figure 15:
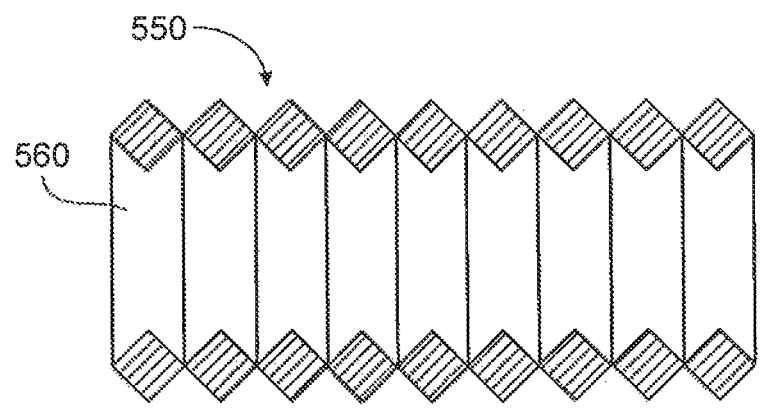
FIG. 15 is a side cross-sectional view of an embodiment of an embolic coil.

As another example, while embolic coils formed of a wound ribbon having a rectangular transverse cross-section have been described, in some embodiments, a ribbon with a different transverse cross-section can be used to form an embolic coil. As an example, FIG. 14 shows a side cross-sectional view of an embolic coil 500 formed of windings of a ribbon 510. As shown in FIG. 14, ribbon 510 has a square transverse cross-section having a length L4 and a width W3 that are equal to each other. As another example, FIG. 15 shows a side cross-sectional view of an embolic coil 550 formed of windings of a ribbon 560. As shown in FIG. 15, ribbon 560 has a diamond-shaped transverse cross-section.

Figure 16:
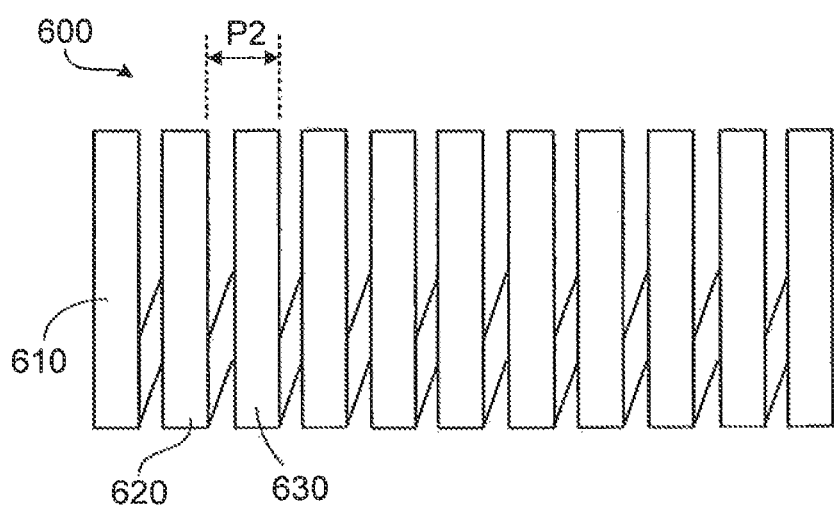
FIG. 16 is a side view of an embodiment of an embolic coil.

As an additional example, in some embodiments, an embolic coil may include consecutive windings that do not contact each other. In certain embodiments, an embolic coil may be formed entirely of windings that do not contact each other. For example, FIG. 16 shows an embolic coil 600 formed of windings of a ribbon 610. As shown in FIG. 16, consecutive windings of ribbon 610, such as windings 620 and 630, do not contact each other. In some embodiments, consecutive windings of ribbon 610 can have a space between them of at least 0.0005 inch (e.g., at least 0.001 inch, at least 0.002 inch, at least 0.003 inch, at least 0.004 inch) and/or at most 0.005 inch (e.g., at most 0.004 inch, at most 0.003 inch, at most 0.002 inch, at most 0.001 inch). Embolic coil 600 has a pitch P2. In certain embodiments, pitch P2 can be at least 0.0015 inch (e.g., at least 0.002 inch, at least 0.003 inch, at least 0.004 inch) and/or at most 0.005 inch (e.g., at most 0.004 inch, at most 0.003 inch, at most 0.002 inch). While windings of embolic coil 600 have approximately the same amount of space between them, in some embodiments, an embolic coil can be formed of a wound ribbon having windings with different amounts of space between them. The space between consecutive windings in an embolic coil can be used, for example, to accommodate a material that enhances thrombosis, such as fibers that enhance thrombosis.

Figure 17:
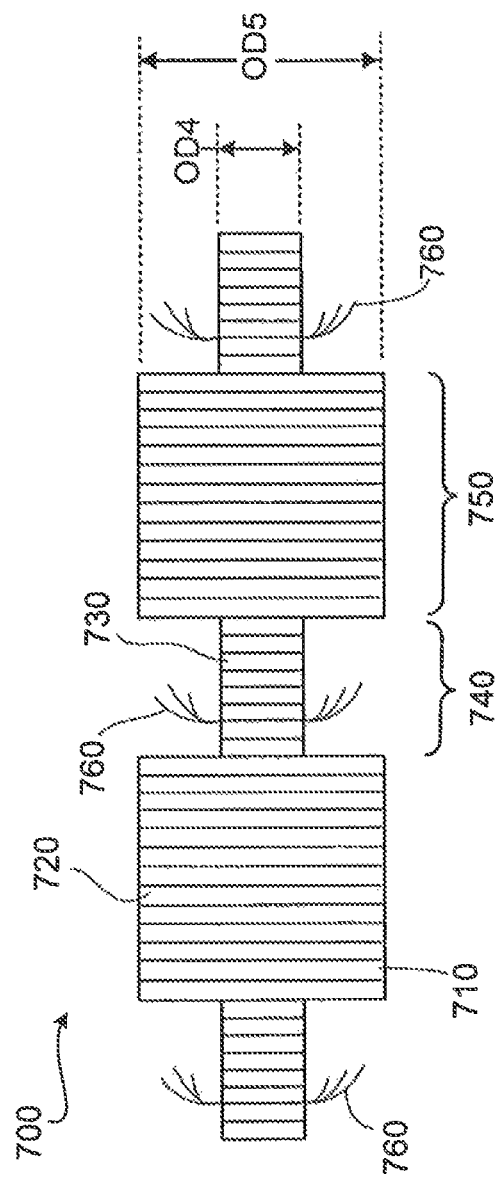
FIG. 17 is a side view of an embodiment of an embolic coil.

As a further example, in some embodiments, an embolic coil can have at least two (e.g., three, four, five, 10, 15, 20) different outer diameters. For example, FIG. 17 shows an embolic coil 700 formed of windings of a ribbon 710, such as windings 720 and 730. Embolic coil 700 includes regions 740 of relatively small outer diameter and regions 750 of relatively large outer diameter. In some embodiments, embolic coil 700 can be formed by winding a ribbon around a mandrel having at least two different outer diameters. In certain embodiments, embolic coil 700 can be formed by winding a ribbon around a mandrel and then grinding down certain regions of the ribbon to reduce the thickness of the ribbon in those regions, thereby forming regions of relatively small outer diameter.

In regions 740, embolic coil 700 has an outer diameter OD4. In some embodiments, outer diameter OD4 can be at least 0.01 inch (e.g., at least 0.02 inch) and/or at most 0.03 inch (e.g., at most 0.02 inch). In regions 750, embolic coil 700 has an outer diameter OD5. In certain embodiments, outer diameter OD5 can be at least 0.015 inch (e.g., at least 0.025 inch) and/or at most 0.035 inch (e.g., at most 0.025 inch). Embolic coil 700 further includes fibers 760 that are disposed between windings of ribbon 710 in regions 740 of relatively small outer diameter. Because fibers 760 are located in regions 740 of relatively small outer diameter, in some embodiments, embolic coil 700 can be accommodated within a delivery device (e.g., a catheter) with a relatively low likelihood of substantial contact between fibers 760 and the walls of the delivery device. This can be advantageous, for example, because if fibers 760 come into sufficient contact with the walls of the delivery device, then fibers 760 can adhere to the walls, which can complicate the delivery of embolic coil 700 from the delivery device (e.g., to a target site). While embolic coil 700 is shown as including fibers, in some embodiments, an embolic coil having at least two different outer diameters may not include any fibers. Embolic coils having at least two different outer diameters are described, for example, in Elliott et al., U.S. patent application Ser. No. 11/000,741, filed on Dec. 1, 2004, and entitled "Embolic Coils", which is incorporated herein by reference.

As another example, while embodiments have been shown in which the pitch of an embolic coil is substantially the same in different regions of the embolic coil, in certain embodiments, the pitch of an embolic coil can differ in different regions of the embolic coil. For example, some regions of an embolic coil can have a pitch of 0.002 inch, while other regions of an embolic coil can have a pitch of 0.004 inch.

As an additional example, while a pushable embolic coil has been shown, in some embodiments, an embolic coil can alternatively or additionally be a detachable embolic coil. For example, the embolic coil can be temporarily attached to a pusher wire. The embolic coil can be, for example, mechanically detachable and/or chemically detachable. In some embodiments, the embolic coil can be electrolytically detachable. In certain embodiments, the embolic coil can be a Guglielmi Detachable Coil (GDC) or an Interlocking Detachable Coil (IDC). Detachable embolic coils are described, for example, in Twyford, Jr. et al., U.S. Pat. No. 5,304,195, and Guglielmi et al., U.S. Pat. No. 5,895,385, both of which are hereby incorporated by reference.

As a further example, in some embodiments, a saline flush can be used to deliver an embolic coil from a delivery device. In certain embodiments, the saline flush can be used in conjunction with a pusher wire.

As another example, in some embodiments, multiple (e.g., two, three, four) embolic coils can be delivered using one delivery device.

As an additional example, in certain embodiments, a treatment site can be occluded by using embolic coils in conjunction with other occlusive devices. For example, embolic coils can be used with embolic particles such as those described in Buiser et al., U.S. Patent Application Publication No. US 2003/0185896 A1, published on Oct. 2, 2003, and in Lanphere et al., U.S. Patent Application Publication No. US 2004/0096662 A1, published on May 20, 2004, both of which are incorporated herein by reference. In some embodiments, embolic coils can be used in conjunction with one or more embolic gels. Embolic gels are described, for example, in Richard et al., U.S. Patent Application Publication No. US 2006/0045900 A1, published on Mar. 2, 2006, and entitled "Embolization", which is incorporated herein by reference.

Figure 18:
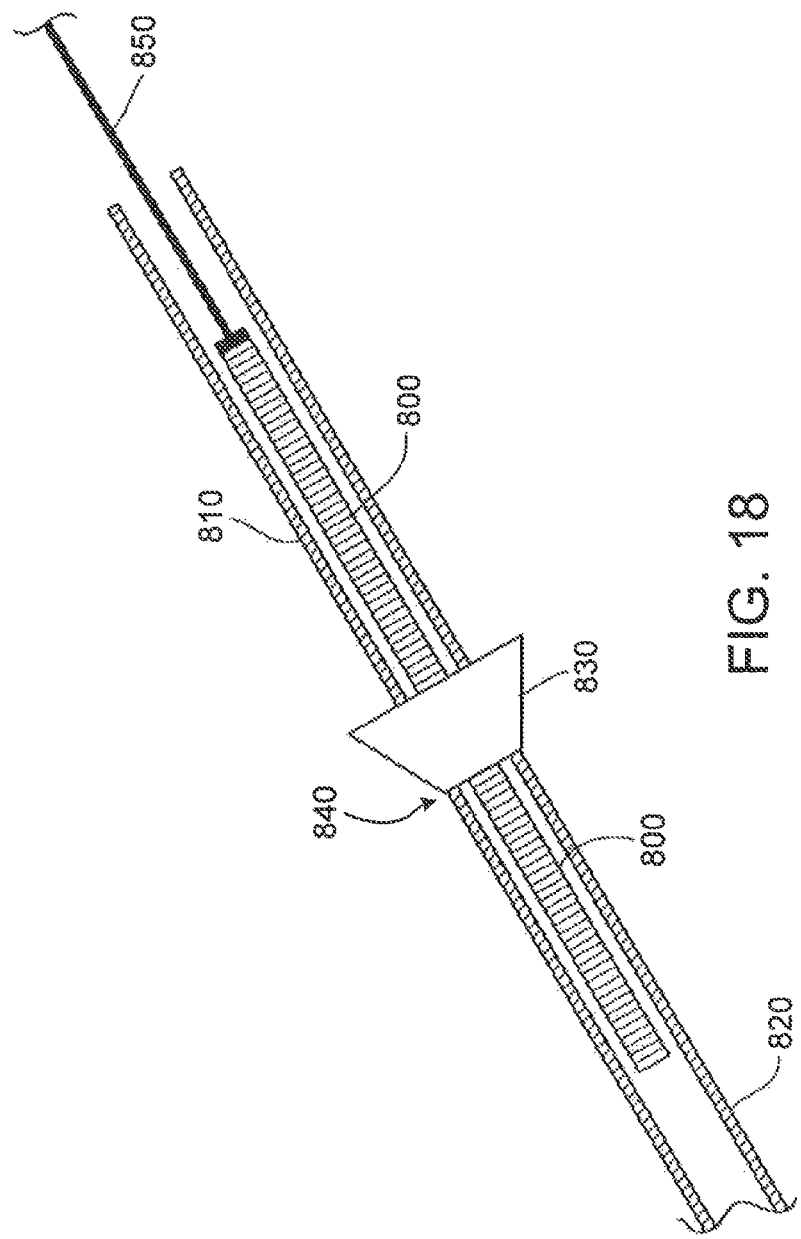
FIG. 18 illustrates the delivery of an embodiment of an embolic coil from an introducer sheath into a delivery device.

As another example, in certain embodiments, an embolic coil can be loaded into a delivery device using an introducer sheath. For example, FIG. 18 illustrates the transfer of an embolic coil 800 from an introducer sheath 810 into a catheter 820. A hub 830 located at the proximal end 840 of catheter 820 directs the placement of introducer sheath 810. After introducer sheath 810 has been placed in hub 830, a pusher 850 is used to push embolic coil 800 out of introducer sheath 810 and into catheter 820.

As an additional example, in some embodiments, an embolic coil can include one or more radiopaque markers. The radiopaque markers can, for example, be attached to one or more windings of the embolic coil.

Other embodiments are in the claims.

What is claimed is:

1. A flat metallic wire ribbon in the shape of an embolic coil, the ribbon having a first side with a first thickness and a second side with a second thickness different from the first thickness wherein consecutive windings are flush with one another.

2. The ribbon of claim 1, wherein the first thickness is larger than the second thickness, and the first side faces the outside of the embolic coil.

3. The ribbon of claim 1, wherein the first thickness is larger than the second thickness and the second side faces the outside of the embolic coil.

4. The ribbon of claim 1 further comprising at least one fiber disposed between at least two windings of the ribbon.

5. The ribbon of claim 1, wherein the ribbon forms a first shape that is a substantially spiral shape characterized by an outer diameter and a second shape characterized by a maximal cross-sectional dimension in an unconstrained state that is greater than the outer diameter of the first shape.

6. The ribbon of claim 1, wherein the shape is selected from the group consisting of a spiral, a single apex vortex, a dual apex vortex, a J, and a complex helical shape.

7. An embolic coil, comprising:
a first outer region comprising a plurality of windings, the first region characterized by a first outer diameter; and
a second region comprising a plurality of windings, the second region characterized by a second outer diameter different from the first outer diameter.

8. The embolic coil of claim 7, wherein each of the first and second regions are formed by a plurality of windings of a wire.

9. The embolic coil of claim 7, wherein at least one of the first and second regions repeats over a length of the embolic coil.

10. The embolic coil of claim 7, wherein at least one of the first and second regions further comprises at least one fiber disposed between at least two windings of a ribbon.

11. The embolic coil of claim 7, wherein the embolic coil is formed from a flat metallic wire ribbon having a first side with a first thickness and a second side with a second thickness different from the first thickness.

12. A flat metallic wire ribbon in the shape of an embolic coil, the ribbon having a first side with a first thickness and a second side with a second thickness different from the first thickness wherein the embolic coil has a pitch equal to the first thickness of said ribbon.

\* \* \* \* \*